United States Patent [19]

Erbe

[11] Patent Number: 5,681,872
[45] Date of Patent: Oct. 28, 1997

[54] BIOACTIVE LOAD BEARING BONE GRAFT COMPOSITIONS

[75] Inventor: Erik M. Erbe, Berwyn, Pa.

[73] Assignee: Orthovita, Inc., Malvern, Pa.

[21] Appl. No.: 568,812

[22] Filed: Dec. 7, 1995

[51] Int. Cl.⁶ .............................. A61K 6/06; C08K 3/40
[52] U.S. Cl. ........................ 523/114; 523/113; 523/115; 524/456; 524/414; 260/998.11; 106/35; 106/634; 106/691; 501/70
[58] Field of Search .............................. 523/114, 115, 523/113; 524/456, 414; 260/998.11; 106/35, 634, 691; 501/70

[56] References Cited

U.S. PATENT DOCUMENTS

| | | | |
|---|---|---|---|
| 2,920,971 | 1/1960 | Stookey et al. | 106/39 |
| 3,629,187 | 12/1971 | Waller | 523/115 |
| 3,981,736 | 9/1976 | Broemer et al. | 106/39.6 |
| 4,110,184 | 8/1978 | Dart et al. | 204/159.23 |
| 4,239,113 | 12/1980 | Gross et al. | 206/568 |
| 4,369,262 | 1/1983 | Walkowiak et al. | 523/109 |
| 4,396,476 | 8/1983 | Roemer et al. | 204/159.16 |
| 4,411,625 | 10/1983 | Kbolitz et al. | 433/217 |
| 4,491,453 | 1/1985 | Koblitz et al. | 433/217 |
| 4,643,982 | 2/1987 | Kasuga et al. | 501/8 |
| 4,652,534 | 3/1987 | Kasuga | 501/5 |
| 4,698,373 | 10/1987 | Tateosian et al. | 522/95 |
| 4,775,646 | 10/1988 | Hench et al. | 501/2 |
| 4,801,528 | 1/1989 | Bennett | 433/220 |
| 4,851,046 | 7/1989 | Low et al. | 106/35 |
| 4,886,843 | 12/1989 | Walton | 522/174 |
| 5,145,520 | 9/1992 | Kokubo et al. | 106/35 |
| 5,204,106 | 4/1993 | Schepers et al. | 424/423 |
| 5,236,458 | 8/1993 | Ducheyne et al. | 623/16 |
| 5,238,491 | 8/1993 | Sugihara et al. | 106/35 |
| 5,336,642 | 8/1994 | Wolcott | 501/3 |
| 5,527,836 | 6/1996 | Yamamoto et al. | 523/114 |

FOREIGN PATENT DOCUMENTS

| | | |
|---|---|---|
| 2208236 | 2/1972 | Germany. |
| 62-010939 | of 1987 | Japan. |
| WO 93/16738 | 9/1993 | WIPO. |

OTHER PUBLICATIONS

W.F. Brown Solubilities of Phosphate & Other Sparingly Soluble Compounds *Environmental Phosphorous Handbook*, Ch. 10 1973.

Vuillemin et al. Fixationof Bone Fragments with BIOCHEM *Arch. Otolygol. Head Neck Surg.* 1987 113:836–840.

Saito et al. Experimental Studies on a new bioactive bone cement; hydroxyapatite composite resin *Biomaterials* 1994 15:156–160.

Zamora et al. abstract Spring 1995 meeting of the American Chemical *Society Bioglass Reinforced Dental Composites: Thermal Mechanical Properties* (1995).

Tamura et al. Bioactive bone cement: The effect of amounts of glass powder and histologic changes with time *Journal of Biomedical Materials Research* 1995 29:551–559.

Dickens–Venz et al. Physical and Chemical properties of resin–reinforced calcium phosphate cements *Dent. Mater.* 1994 10:100–106.

Meechan et al. Adhesion of composite resin to bone—a pilot study *British Journal of Oral and Maxillofacial Surgery* 1994 32:91–93.

Sahama et al Gozenite and comeite, two new silicates from the Belgian Congo *Mineral. Mag.* 1957 31:503–511.

*Introduction to Ceramics* 2nd Ed., p. 528, John Wiley & Sons 1976 W.D. Kangery.

BD Cullity, *Elements of X–ray Diffraction*, 2nd Ed., pp. 409–419, Addison–Wesley (1978).

*Primary Examiner*—Andrew E. C. Merriam
*Attorney, Agent, or Firm*—Woodcock Washburn Kurtz Mackiewicz & Norris LLP

[57] ABSTRACT

Novel fillers comprising combeite glass-ceramic are provided. hardenable restorative compositions comprising particulate combeite glass-ceramic provide improved biocompatibility in bone restorations. Hard, shaped bodies for orthopaedic, dental and other uses are also provided.

40 Claims, 4 Drawing Sheets

BIOACTIVE LOAD BEARING BONE GRAFT COMPOSITIONS

FIELD OF THE INVENTION

This invention provides novel, bioactive, load bearing, hardenable compositions, especially bone grafting compositions. In accordance with preferred embodiments, glass-ceramic reinforced resin matrix composites are provided which are, at once, deliverable, shapable, and able to adhere to metal, ceramic, and natural bone tissue. Preferred composites of the present invention are capable of bearing significant loads while remaining highly compatible with natural bone tissue. The compositions of the present invention are amenable to orthopaedic and dental uses in a number of contexts. Novel filled composites are employed comprised of novel inorganic fillers. Such fillers comprise combeite. Hard, shaped bodies are also provided.

BACKGROUND OF THE INVENTION

The need for biomaterials in orthopaedic and dental applications has increased as the world population ages. A significant amount of research into biomaterials for orthopaedic and dental uses has attempted to address the functional criteria for orthopaedic and dental reconstruction within the human body. The materials which have become available for such uses have improved in recent years. All such materials must be biocompatible, however, and the degree of biocompatibility exhibited by materials which are candidates for such use is always a major concern. Biomaterials useful for orthopaedic and dental reconstructions must have high strength, must be able to be immediately affixed to the situs for reconstruction, must bond strongly to bone, and must give rise to strong, highly resilient restorations.

Among the materials which have been used for orthopaedic and dental restorative purposes are bone cements based upon acrylic species such as polymethyl methacrylate (PMMA) and related compositions. Such materials usually are capable of convenient delivery to the site of restoration and can be formed as to be moldable and to have reasonable degrees of affinity for bony tissue. PMMA cements, however, lack bioactivity and the ability to generate the formation of bone tissue. The inertness of such restoratives leads to micromotion and fatigue over time with attendant aseptic loosening. Additionally, the polymerization of PMMA-based materials can give rise to significant exothermicity which can lead to localized tissue necrosis and inflammation. Moreover, residual methyl methacrylate monomer can leech into surrounding tissue leading to site inflammation and implant failure. Implants formed from PMMA-based materials can also give rise to particulate debris, inflammation, and failure. PMMA polymeric structures are generally two-dimensional and limited as to strength.

Bone grafts using bioactive glasses and calcium phosphates, collagen, mixtures and the like have good biocompatibility and give rise to bone tissue formation and incorporation in some cases. However, prior graft materials lack the desired load bearing strength and are generally technique sensitive.

Prior attempts to improve such bone grafting material through the development of self-setting calcium phosphate cements as well as glass ionomer bone cements have shown promise. Both materials can be bioactive in some cases and both can exhibit considerable strength. Glass ionomers, in particular, have enjoyed success in dental applications. However, most of the strengths of glass ionomer composites is achieved by reacting a fluoroaluminosilicate glass with a polyalkenoic polymer matrix. Carboxyl functionalities exist on the polymer backbone, which functionalities chelate with ions in the surface bone material. The usual time for a surface active biomaterial to form an inner active layer with inner tissue is from six to eight weeks. If the material's function relies upon this interactive biolayer rather than its inherent strength, the required reaction time can lead to premature failure of the material.

A number of different glasses, glass-ceramics, and crystalline phase materials have been used, either alone or in combination with acrylic polymerizable species, and other families of polymers, for restorative purposes. These include hydroxyapatite, fluorapatite, oxyapatite, Wollastonite, anorthite, calcium fluoride, agrellite, devitrite, canasite, phlogopite, monetite, brushite, octocalcium phosphate, Whitlockite, tetracalcium phosphate, cordierite, and Berlinite. Representative patents describing such uses include U.S. Pat. Nos. 3,981,736, 4,652,534, 4,643,982, 4,775,646, 5,236,458, 2,920,971, 5,336,642, and 2,920,971. Additional references include Japanese Patent No. 87-010939 and German Patent OS 2,208,236. Other references may be found in W. F. Brown, "Solubilities of Phosphate & Other Sparingly Soluble Compounds," *Environmental Phosphorous Handbook*, Ch. 10 (1973). All of the foregoing are incorporated herein by reference to provide disclosure, inter alia, of prior restorative materials and methods and compositions which may be included in the compositions and methods of the invention, as well as, methods which may be employed as part of or ancillary to the invention.

In addition to the foregoing, certain animal derived materials, including coral and nacre, have also been used in biomaterials for restorative purposes.

U.S. Pat. No. 4,239,113 to Gross et al. reports a pliable, moldable acrylic-based bone cement reinforced with from 15 to 75% by weight of a bioactive glass together with between 1 and 10% by weight of vitreous mineral fibers. The disclosed function of the glass fillers and fibers is to impart mechanical strength to the acrylic matrix, however this advantage diminishes as the fibers degrade over time in the body. Most of the problems associated with the use of polymethyl methacrylate still exist in the materials disclosed by Gross.

Vuillemin et al. in *Arch. Otolygol. Head Neck Surg.* Vol 113 pp. 836–840 (1987) introduced different bioactive fillers such as tricalcium phosphate and bioceramic $A_2$ into bisphenol-A-diglycidyl methacrylate (bis GMA) polymerizable through the action of peroxide systems such as benzoyl peroxide mixed with amines. Use in human subjects for successful treatment of a right frontal sinus and a supraorbital edge was shown in a frontobasal skull fracture. Both examples were primarily non-load bearing, however.

Two component, resin composites containing both salicylates and acrylates, cured through a calcium hydroxide cement reaction is described by Walton in U.S. Pat. No. 4,886,843. The use of calcium hydroxide as a filler results in $Ca^{2+}$ ion release for the remineralization of dental tissues while filling tooth restorations. Adherence to tooth structure was shown together with maintenance of strength and permeability for the reaction of the calcium hydroxide filler.

Kokubo et al. in U.S. Pat. No. 5,145,520 discloses a powder-liquid mixture yielding a bioactive cement. Fine glass powder comprising a apatite-Wollastonite glass-ceramic, is reacted with an aqueous solution of ammonium phosphate. The resulting, hardening cement was employed to repair bone and as a dental restorative cement. The cement was said to harden quickly to a high strength material with no heat generation during its setting.

Sugihara et al., in U.S. Pat. No. 5,238,491, discloses a powder-liquid hardening dental material. This material uses tricalcium phosphate or tetracalcium phosphate as a main constituent together with a hardening liquid comprising of at least one inorganic acid such as acetic acid. An addition of collagen is used to aid in biocompatibility and hydroxyapatite formation. One disclosed goal is biocompatibility together with chemical bonding and space filling of adjacent tissues.

PCT document WO 93/16738—Yamamuro et al. describes a bioactive cement deriving from a bioactive glass-filled resin matrix composite. The glass is a non-alkali-containing calcium oxide-silica-$P_2O_5$-magnesium oxide-calcium fluoride loaded into a resin matrix, bisphenol-A glycidyl dimethacrylate, polymerized in two separate pastes, one containing benzoyl peroxide and one N, N-dimethyl-p-toluidine. The interaction of the fillers with the resin was said to be significant, giving rise to a good physiological environment for the achievement of bioactive composites having high strength, low heat generation, and good bonding capability.

Saito et al., in *Biomaterials* Vol 15 No. 2 (1994), used bisphenol-A glycidyl dimethacrylate together with amine-peroxide catalyst as a resin matrix to be filled with hydroxyapatite granules having average size of approximately 2 micrometers. This material was said to show good strength as a bone cement (compressive strength of 260 MPa), along with good bioactivity and bone formation in the bonding of femoral condyles of rabbits after eight weeks. The cement was also said to have a low exotherm of polymerization.

Zamora et al., in an abstract submitted for the Spring 1995 meeting of the American Chemical Society entitled *Bioglass Reinforced Dental Composites: Thermal Mechanical Properties*, describe a heat polymerized bisphenol-A glycidyl dimethacrylate matrix reinforced with Bioglass™ (described below). It was suggested that the bis GMA resin matrix gives significantly lower exotherms of polymerization than polymethyl methacrylate.

Tamura et al., in *Journal of Biomedical Materials Research* Vol. 29 pp 551–559 (1995), discloses the effect of the amount of filler loading an a bioactive bone cement. Apatite-Wollastonite glass-ceramic filler, together with a bisphenol-A glycidyl dimethacrylate matrix resin was employed in weight ratios of 30, 50, 70, and 80%. Animal studies were said to show that bioactivity increases as the bioactive filler was increased, however the mechanical properties did not necessarily follow the same trend.

Dickens-Venz et al., in *Dent. Mater.* Vol. 10 pp 100–106 (1994), report on the physical and chemical properties of resin-reinforced calcium phosphate cements.

Meechan et al., in *British Journal of Oral and Maxillofacial Surgery* Vol. 32 pp. 91–93 (1994), disclose a pilot study analyzing the adhesion of composite resins to bone using commercially available dental materials.

Roemer et al., in U.S. Pat. No. 4,396,476, disclose interpenetrating polymer networks in hardenable compositions for a number of uses including the filling of teeth and bone.

U.S. Pat. No. 4,369,262—Walkowiak et al. discloses dental materials based upon filled cross-linked plastics together with polymerizable binders.

U.S. Pat. No. 4,110,184—Dart et al. discloses photocurable dental filling compositions based on modified, filled acrylic polymerizable materials.

Bioglass™ is believed to be described in U.S. Pat. No. 4,851,046—Low et al. Low et al. describe a biocompatible glass, known to those skilled in the art as 45S5 bioactive glass, in particular particle size distributions to facilitate admixture with blood for repair of periodontal defects. Bone tissue ingrowth peripheral to the repair is disclosed. The materials disclosed by Low et al. are not significantly load bearing, however.

U.S. Pat. No. 5,204,106—Schepers et al. discloses improved methods for forming osseous tissue from bioactive glass such as 45S5 glass. Critical particle sizes permit osteogenesis throughout a restoration. The disclosed compositions are not highly load bearing.

While a number of materials have been shown to be useful for the filling of bone and for use in restorative dentistry, there is still a significant need for improved materials for such uses. Thus, there remains a long-felt need for restorative compositions comprising resin matrixes together with bioactive fillers which have the desired combination of delivery viscosity, setting conditions, setting strength, and bioactivity, combined with great overall strength and long-term compatibility with bone and other tissue. It is also greatly desired to achieve stable, strong, biocompatible restorations in a short time period, shorter than the up to eight weeks which can be required with prior materials.

It is, therefore, a principal object of the present invention to provide improved bone restorative materials having immediate physical strength and biocompatibility.

A further object of the invention is to provide load bearing bone grafting composite materials for use in diverse restorative circumstances within the human body.

Yet another object of the invention is to provide materials having rapid adherence to implants and bone tissue together with the achievement of elastic moduli which are close to the modulus of bone.

A still further object is to achieve bone grafting composites which can give rise to an active resin-calcium oxide-phosphorus oxide gel layer which is capable of enhancing the toughness and long term mechanical stability of restorations employing such materials.

Another object of the invention is to improve implant fixation in dentistry and orthopaedics through the improved physical and physiochemcial relationship of materials of the present invention, natural bone, and implant materials.

A further object of the invention is to incorporate certain drugs into the compositions hereof so as to confer the benefits of such drugs upon the situses of restoration employing such materials.

Still another object is to provide hardened, shaped bodies of bioactive material for orthopaedic and dental use.

It is also an object of the invention to provide bone grafting materials and cements which are capable of immediate placement together with concomitant load bearing ability as well as ensuing bioactivity giving rise to the formation of natural bony tissue.

Other objects will be apparent from a review of the specification and attendant claims.

SUMMARY OF THE INVENTION

In accordance with the present invention, hardenable compositions are provided comprising a polymerizable matrix and inorganic filler. At least 10% of the inorganic filler comprises a combeite glass-ceramic having a least 2% by volume of regions of combeite together with irregular morphology. Combeite is a mineral having chemical composition $Na_4Ca_3Si_6O_{16}(OH)_2$ which was first reported as a mineral from the Belgian Congo in 1957. It has now been found that the employment of inorganic fillers in restorative compositions, which fillers include crystallites of combeite in a glass-ceramic structure (hence, combeite glass-ceramic) in accordance with the present invention gives rise to superior orthopaedic and dental restorations.

It is preferred that the combeite glass-ceramic which forms some or all of the fillers of the present invention comprise at least about 2% by volume of combeite. Higher percentages of combeite are more preferred and volume percentage between 5–50% of combeite are particularly desired. It will be appreciated that the combeite glass-ceramic particles of the present invention are heterogenous in that they comprise a glassy, amorphous structure having crystallites or regions of crystallinity of combeite dispersed therethrough. It is preferred that these heterogenous particles of combeite glass-ceramic have particle sizes greater than 0.1 micron, with somewhat larger sizes being preferred. Particle sizes between about 0.2 and 300 microns are more preferred.

In accordance with the invention, combeite glass-ceramic particles having irregular morphologies are greatly preferred to attain the beneficial results of the invention. Thus, while it could be proposed to provide combeite glass-ceramics having relatively smooth particulate forms, such regular morphologies are not preferred. Preferred particles may be conveniently obtained through the methods of preparing such combeite glass ceramics as set forth in the present invention.

In accordance with some preferred embodiments, blends of combeite glass-ceramics may be useful. Thus, a number of different combeite glass-ceramics can be prepared having different properties, such as combeite crystallite size, percentage of combeite, particle sizes of the filler and the like, and the resulting combeite glass-ceramics blended to form fillers for restorative compositions. It is also preferred in some cases to admix combeite glass-ceramic fillers in accordance with the present invention with other fillers which are consistent with the objectives to be obtained. Thus, a wide variety of such other fillers may be so employed so long as at least 10% by weight of the overall inorganic filler of the hardenable compositions of the invention comprise combeite glass-ceramic.

The hardenable composition of the invention also comprise a polymerizable matrix. A very large number of polymerizable species have been known heretofore for use in the formulation of restorative compositions of orthopaedics and dentistry. While certain preferred polymerizable species have been found to be particularly useful in the hardenable compositions of this invention, it is to be understood that any of the polymerizable species known to persons of ordinary skill in the art for use in conjunction with orthopaedic and/or dental restoration may be used herein. In particular, a wide variety of a polymerizable acrylic species may be employed, however those based upon bisphenol-A, such as bisphenol-A dimethacrylate and related species are preferred. Bisphenol-A glycidyl dimethacrylate is especially suitable for biological restorations for all of reasons known to persons skilled in the art and such is preferred here.

Catalytic agents to effect polymerization are also known to persons skilled in the art and any of those catalytic agents and/or systems may be employed in the present invention. In general, "heat-curable" and photopolymerizable systems have found wide utility. Thus, a number of peroxides, such as benzyl peroxide can be used in "heat curable" formulations, and such is preferred for embodiments of the present invention. Photopolymerization is also useful, especially visible light curing. Camphoroquinone is a well-regarded visible light curing catalyst especially when admixed with a tertiary amine.

It is preferred that the materials of the present invention be amenable to delivery in convenient fashion. Exemplary methods of delivery include syringes, such as wide mouth syringes and spatulation. Accordingly, viscosities for the hardenable composition of the present invention between about 5,000 and 75,000 centipoises is preferred. Still more preferred are viscosities between about 7,500 and 60,000 centipoises.

In accordance with certain embodiments of the present invention, methods are provided for the restoration of bony tissue. In this regard, an area of bony tissue requiring repair as a result of disease, injury, desired reconfiguration, or otherwise is surgically prepared and a composition of the present invention introduced into the situs for the repair. The composition is caused to polymerize through either heat or photochemistry, the wound closed, and the restoration allowed to heal.

A major advantage of the restoration, after polymerization, has a significant, inherent strength such that restoration of load-bearing bony situses can be had. While immobilization of the effected part will likely still be required, the present invention permits the restoration of many additional bony areas than heretofore. Further, since the combeite glass-ceramic and other fillers of the present invention are biocompatible and, indeed, bioactive, osteogenesis occurs. This leads to bone infiltration and replacement of the formed $CaO-P_2O_5$ surface layer with autologous bone tissue. Superior restoration ensues.

The invention also provides methods for the preparation of bioactive, inorganic, particulate fillers comprising combeite glass-ceramics. Appropriate minerals are melted together for a time and under conditions effective to achieve substantial homogeneity and to form a melt. The minerals which are melted together, conventionally silica, sodium oxide, calcium carbonate, and calcium phosphate, are blended in an amount so as to give rise to the combeite glass-ceramics as required herein. When a homogenous melt has been obtained, the melt is either cooled on an inert substrate or quenched in distilled water. If cooled on an inert substrate, the resulting slab or body of material is subsequently comminuted through crushing and the like to form a particulate material. If quenched in water, the melt forms a frit, which is easily shattered into particles. In either event, the particles are reduced in size as may be necessary and sorted through sieving or otherwise. The particles are then selected, preferably tested to ensure that proper size ranges, combeite content, and other properties are-present and either used alone or blended with compatible materials to form inorganic fillers for the production of bioactive restorative compositions.

It will be understood that the fillers in accordance with the present methods of manufacture thereof are not necessarily limited to use in hardenable compositions and polymerizable matrices. Rather, such fillers are novel per se and may be used in any composition, either for orthopaedic restoration, dental restoration, or otherwise. Thus, such fillers can be used in medical and non-medical articles, such as golf balls, should the same be desired.

Through the present processes, fillers will have irregular morphologies rather than the smooth morphologies which would be expected to be obtained through some other possible techniques. Such irregularities can be macroscopic, on the same scale as particle size, not just microscopic.

The hardenable compositions of the present invention may also be elaborated into hardened, shaped bodies for a number of uses. Thus, orthopaedic appliances such as joints, rods, pins, or screws for orthopaedic surgery, plates, sheets, and a number of other shapes may be formed through processing in accordance with methods known to persons of ordinary skill in the art. Such hardened compositions can be bioactive and can be used, preferably in conjunction with hardenable compositions in accordance with the present invention in the form of gels, pastes, or fluids, in surgical techniques. Thus, a screw or pin can be inserted into a broken bone in the same way that metal screws and pins are currently inserted, using conventional bone cements or restoratives in accordance with the present invention or otherwise. The bioactivity of the present hardenable materials will give rise to osteogenesis with beneficial medical or surgical results.

BRIEF DESCRIPTION OF THE DRAWINGS

FIG. 3b shows a vertebral implant for spine fusion, while FIG. 3c depicts an orthopaedic screw. An endodontic "point" is shown in FIG. 3d.

DETAILED DESCRIPTION OF PREFERRED EMBODIMENTS

The present invention provides hardenable restorative compositions including inorganic fillers having, as a constituent, combeite glass-ceramic. It has been found that significant quantities of combeite in glass-ceramic particles impart highly beneficial properties to restorative compositions including such particles. In particular, good biocompatibility, osteogenesis, radiopacity, workability, and other properties are conferred through the use of combeite glass-ceramic as all or part of inorganic filler material in hardenable, restorative compositions.

Combeite, which is $Na_4Ca_3Si_6O_{16}(OH)_2$, was discovered in 1957 in natural deposits in the Belgian Congo, as reported by Sahama et al, *Mineral. Mag.* Vol. 31, No. 238, page 503 (1957). Combeite has not been considered a commercially significant material heretofore. It has now been found, however, that in the preparation of certain inorganic materials based upon "45S5" glass, some combeite may form. Indeed, in the preparation of Biogran™ restorative composition, which is a filling material sold by the Orthovita company of Malvern, Pa. for the restoration of osseous defects, small quantities of combeite may be formed during the manufacturing process. This has heretofore been considered to be an impurity, and the presence of 2% by volume or more of combeite in the Biogran product, as measured by x-ray spectroscopy has been treated as a quality control defect and cause for product rejection.

It has now been found, however, that the foregoing "impurity" is actually highly beneficial, especially when caused to be present in greater amounts. Thus, when combeite crystallites are fostered in the preparation of 45S5 bioactive glass, such that combeite is present in amounts of at least about 2% by volume and preferably more, beneficial results are obtained.

It is now believed to be highly desirable to permit the growth of combeite crystallites during the preparation of particulate, inorganic filler materials for use in biological restorations, and this may be done through control of the conditions of time and temperature of the formation, cooling, and optional heat treating of such materials.

In accordance with the present invention, a blend of inorganic materials is prepared containing the compositions which will give rise to the inorganic products desired. In particular, it is desired to select starting minerals for the preparation of the combeite glass-ceramics of the present invention which contain the constituent elements of the combeite and of the glass material which will form the amorphous regions surrounding the combeite crystallites. It is greatly preferred to employ minerals giving rise to "45S5" glass, known per se to persons of ordinary skill in the art. U.S. Pat. No. 5,204,106 describes in detail how such glasses can be prepared from constituent, inorganic materials.

The overall constitution of certain preferred inorganic particles in accordance with the present invention, including both the glass portion and the crystallites of combeite, is as follows:

$SiO_2$ from 40 to 55% by weight $Na_2O$ from 10 to 32% by weight $P_2O_5$ from 4 to 12% by weight; and $CaO$ from 10 to 32% by weight.

It is more preferred to prepare particles having overall compositions in accordance with the following:

$SiO_2$ from 42 to 48% by weight $Na_2O$ from 14 to 28% by weight $P_2O_5$ from 5 to 10% by weight; and $CaO$ from 20 to 29% by weight.

As is known to persons of ordinary skill in the art, a particularly useful overall composition for the particles of the present invention has the formula:

$SiO_2$ about 45% by weight $Na_2O$ about 24.5% by weight $P_2O_5$ about 6% by weight; and $CaO$ about 24.5% by weight.

This is the composition which is conventionally known as "45S5" glass.

As will be understood, certain chemical transformations occur upon heating the constituent minerals into a melt during the course of formation of the particles of the present invention. Thus, certain oxidation-reduction reactions take place during melting together with inorganic disproportionation such that the total constituency of the staring materials may be different from that of the product particles. In order to prepare "45S5" glass, it has been conventionally known to employ 33.97% $SiO_2$, 30.98% $Na_2CO_3$, 26.36% $CaCO_3$ and 8.68% $CaHPO_4$; (all percentages by weight). It will be appreciated that other formulations also give rise to the products the present invention and that all such formulations are within its spirit.

In accordance with preferred methods of the present invention, appropriate inorganic starting materials are caused to be melted under conditions of time and temperature sufficient to effect complete disproportionation and oxidation/reduction as may be required and to achieve homogeneity of the melt. The melt is either then cast into an inert form to form a mass or quenched in distilled water to form a frit. In either case, comminution is effected either by crushing, milling or otherwise, and the resulting particles sized, assayed for combeite content, and either used as an inorganic filler or blended for such use.

It will be appreciated that during the processing of the fillers of the present invention, crystallites—small areas of crystallinity—of combeite grow from the melt. The resulting particles are comprised of amorphous, glassy areas together with combeite crystallites dispersed therethrough. Such structures are known per se as glass-ceramics. A combeite glass-ceramic is, therefore, a glassy material having crystallites of combeite therein. For purposes of the present invention, the term "combeite glass-ceramic" should be taken to mean a glass having crystallites of combeite dispersed therethrough which material is also possessed of properties otherwise consistent with the results and objects to be attained hereby. Thus, it is greatly to be preferred that such materials be biocompatible and capable for use as an inorganic filler in hardenable, restorative materials for orthopaedic and dental use.

It is possible to vary the content of combeite crystallites in the combeite glass-ceramics in accordance with the present invention as well as to vary the crystallite size, and other properties. It will be appreciated that when combeite crystallites grow from the substantially homogeneous material of the melt, the remaining glassy areas are depleted in composition as regards the materials comprising the combeite. Thus, in a combeite glass-ceramic, the glassy areas in the combeite crystallites may not have the same composition as the overall combeite glass-ceramic. Indeed, it is possible that the chemical composition of the glassy portion of the particles of the present invention varies from location to location depending upon the relative concentration of combeite crystals locally to those several locations. It is, therefore, necessary to measure the overall chemical composition of the particles of the invention, rather than the composition of the glassy portions at localized areas thereof. In any event, it is preferred to characterize the particles, at least in part, by what they do rather than by what they are. Such particles are comprised of combeite and glassy areas, and are highly biocompatible. They can give rise to osteostimulation or osteogenesis when included as a part of an orthopaedic or dental restoration.

As will be understood by persons skilled in the art, crystallization to form combeite glass ceramic in accordance with the present invention is a process involving nucleation and crystal growth. These two parameters are inherent to a particular system and is determined by the kinetics of time and temperature of that system. Thus, to alter the amount of crystallization, as represented by $V_C$, the volume fraction crystallized, along with the size of the resulting crystals, time and temperature profiles are varied. A higher temperature above the maximum temperature of crystallization, $T_C$, will generally yield larger crystals more rapidly than heating the material below $T_C$. As will also be appreciated by persons of ordinary skill in the art, extending the time at temperature $T_C$ is a simple way to predictably increase the amount of crystal content of a given material. The $T_C$ temperature is easily obtained from the change in intercept of the differential thermal analysis curve for the material, taken in accordance with the standard methods in the art. The degree of crystal nucleus dispersion is governed by the selection of raw materials to some extent and the level of homogeneity in processing. Each of the nuclei around which crystal can grow generates sensible crystals so long as the appropriate chemical composition is available in the "neighborhood" of the nucleus.

In short, it is well within the skill of persons or ordinary skill in the art to vary the crystal content of materials in accordance with the present invention and such persons will have no difficulty in obtaining materials having varying content of crystallites and particle crystallite sizes.

The quenched glass after been annealing and fragmentation can be crystallized by the controlled heating of the glass through the transition temperature to the $T_C$ which is defined by the tangent intercept of the exotherm for the onset of crystallization as measured by differential thermal analysis. This temperature ranges from 660° to 760° C. depending upon heating rate and particle size for this composition and can be raised as high as 1000° C. for more rapid crystallization kinetics. A preferred temperature for combeite formation is 700° C. for 2-4 hours.

Milling and classification of the glass material after crystallization should preferably be done in a dry mill approach. Dry ball milling, impact or puck milling are acceptable means of comminution. Initial quenching to form a frit by water or splat cooling is also useful, assuming the subsequent crystallization profile is adjusted for the different thermal history.

Preferred bioactive glass-ceramics of this invention need not be surface treated, but up to 50% by weight of the filler may be silanized. Silanization can be performed by dispersing the powder into a slurry of acid, e.g. glacial acetic, to effect catalysis of a silane coupling agent such as (3-methacryloxypropyltrimethoxysilane). Preferably at 2 to 10% by weight silane is used.

The particles of the present invention comprising combeite glass-ceramic, when prepared in accordance with the methods of the present invention, have irregular morphologies. Thus, they will be seen to have prominences, declivities, cracks, and other irregularities or otherwise be perceived to be "unsmooth." These irregularities are desirable in that they impart improvements in packability of the filler particles, and improvements in access of biological fluid to the interior of the particles. While it may be possible to prepare combeite glass-ceramics under certain circumstances through techniques such as sol-gel chemistry, which processes will give rise to relatively "smooth" particles, such procedures and the smooth particles they provide are not preferred.

The combeite glass-ceramic particles of the present invention preferably comprise at least about 3% by volume of combeite. It is more preferred that at least about 5% by volume of the combeite glass-ceramic comprise combeite, with at least about 10% being even more preferred. Amounts of combeite between about 5 and 50% by volume and preferably between about 10 and 20% by volume are still more preferred. It will be understood that it is very difficult to measure the combeite content in combeite glass-ceramics on a weight basis. It is, however, possible to closely estimate the volume composition of combeite in combeite glass-ceramics through photomicroscopy using known techniques. For example, in *Introduction to Ceramics*, 2nd Ed., pg 528, John Wiley & Sons (1976), W. D. Kangery explains certain of these optical techniques. It will be understood that a cross-section of a particle will transect the constituent combeite crystallites at various points and that the transection of the combeite crystallite at or near their midline or at a location of a wide dimension will give a relatively large two-dimensional view of the size of that particle. Transection at an apex will suggest that the particle is relatively small. A statistical analysis of the results of such an evaluation, however may be had, thus leading to a good estimate of volume content of combeite in combeite glass-ceramics.

The concentration of combeite in combeite glass-ceramics may also be determined by X-ray diffraction as set forth in BD Cullity, *Elements of X-ray Diffraction*, 2nd Ed., pp 409–419, Addison-Wesley (1978). This technique also gives rise to an understanding of the volume fraction of a material being studied which comprises an element or compound in question. This may be done in number of ways including external standardization, direct comparison, and through use of an internal standard. The determination of volume fraction of combeite and combeite glass-ceramics in accordance with the present invention can be determined by persons of ordinary skill in the art using the education, training and experience enjoyed by such persons.

Figure 1:
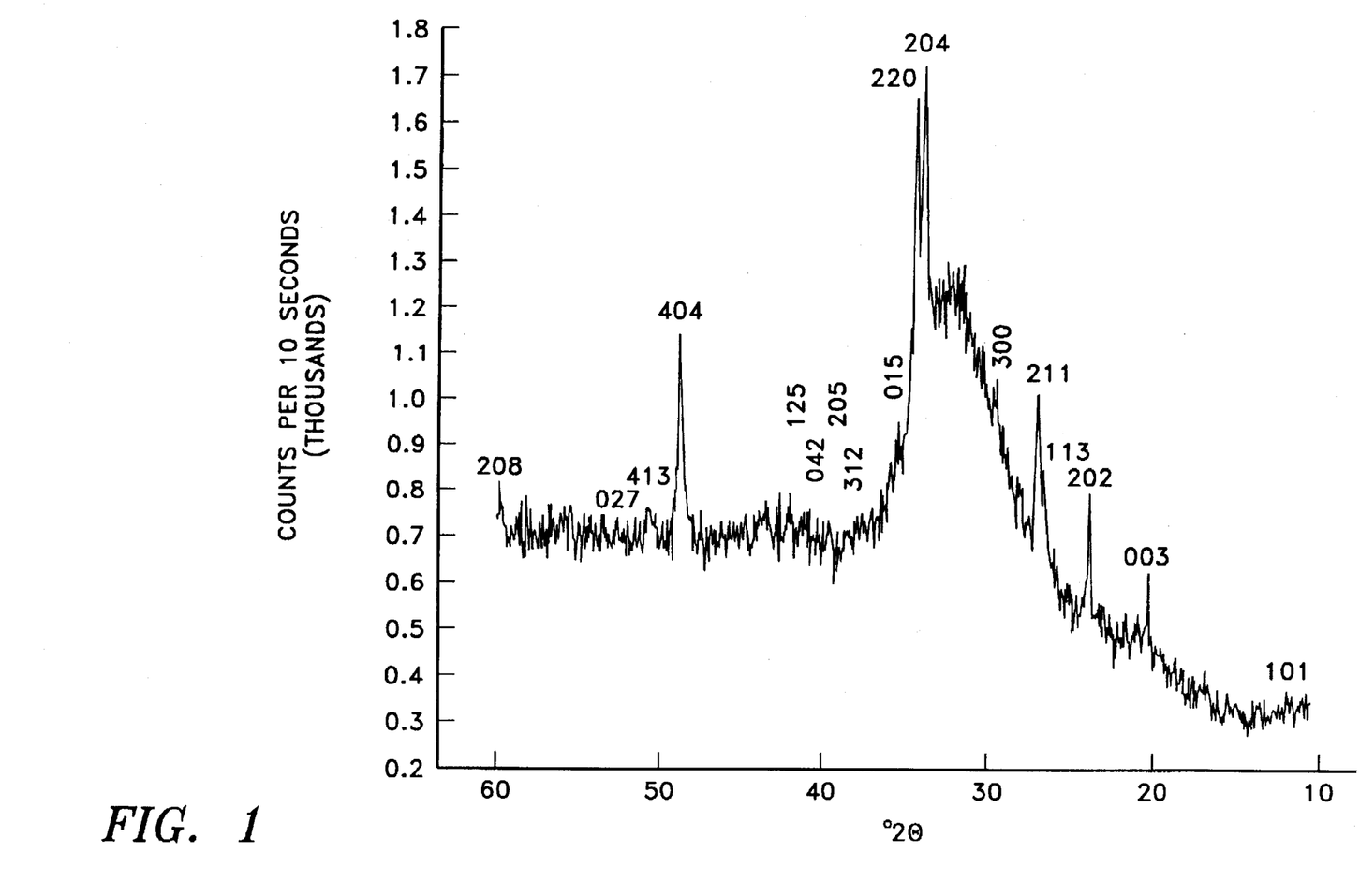
FIG. 1 depicts the X-ray diffraction spectrum of combeite using copper K$\alpha$ at 35 kV and 20 mA at a step interval of 0.05°.

FIG. 1 is a depiction of an X-ray diffraction spectrum of combeite glass-ceramic in accordance with the present invention. The peak positions on the x-ray diffraction curve correspond to the d-spacing between known planes of atoms or indices used to describe specific crystals. The number identifying the H, K, L or Miller indices, correlate to numbered planes. Several specific planes allow determination of a particular crystal phase. One first matches the peak positions in relative intensities of an x-ray diffraction spectrum to be analyzed to a set of power diffraction indices which are generally computerized to identify a particular crystal phase. Once established, calculations can assign specific plane numbers to specific peaks on the x-ray diffraction pattern. Thus, for combeite, the most pronounced planes are 204, 220, 211, 202 and 113.

It is understood that the detection limit for the detection of particular crystals in standard x-ray diffraction instrumentation is from 1 to 2% by weight. Thus, for relatively small amounts of particular crystalline phases in materials, the limitations of the particular instrumentation must always be kept in mind. All of the foregoing considerations are well-known to persons of ordinary skill in the art, however, who will have no difficulty in determining the identity and quantitation of combeite in materials generally in accordance with the present invention from the foregoing discussion.

In general, it is understood that the determination of volume fractions of combeite in the particles of the present invention can be most accurately determined through cross-sectioning as described above. The x-ray diffraction technique, also described above, is very convenient and useful in approximating such volume fraction.

The preferred combeite glass-ceramic particles in accordance with the present invention are such that at least about 95% by weight of said particles have particle sizes greater than about 0.1 microns. It is preferred that at least 95% of such particles have particle sizes greater than about 0.2 microns and that such particles have sizes less than about 300 microns. In accordance with more preferred embodiments, at least 95% of the particles have sizes less than about 100 microns. It is still more preferred that at least 95% of the particles have particle sizes between about 0.2 and 300 microns with size between about 0.2 and 100 microns being still more preferred. In accordance with other preferred embodiments, at least 95% of the particles, by weight, have particles sizes between about 0.5 and 50 microns.

The measurement of particle sizes of the combeite glass-ceramics of the present invention may be done in a number of ways. For larger particle sizes, those greater than about 20 microns, it is convenient and customary to determine particle sizes through the use of sieving. The segregation of particles into size ranges through the use of progressively finer sieves is well-known and conventional. It is understood that a distribution of particle sizes will be segregated through this procedure and that particles having average sizes somewhat larger than a nominal size may, nonetheless, pass through a sieve, especially when such particles are irregular as is preferred in the present invention. This is so because elongated particles may slip through a sieve opening in a lengthwise direction. It will accordingly be understood that particle sizes disclosed herein are somewhat inexact for these and other reasons. Nonetheless, it is believed that persons of ordinary skill in the art will have no difficulty in determining appropriate particle sizes for any particular application as may be desired in connection with the present invention.

For particle sizes less than about 10 microns, sieving is generally unproductive in providing size determination. Rather, a determination of particle size through optical means is conventionally employed. Optical particle size counters are well-known and are readily available, e.g. from the Horiba and MicroTrac companies. Additionally difficulties exists in determining particle sizes of small particles through optical means, but resolving problems in this area is well within the skill of persons of ordinary skill in the art.

In accordance with the present invention, it has been conveniently chosen to require that particles have "at least about 95% by weight" of a particular size limitation or size range." It is not desired that this aspect of the invention be limited strictly by a formula, but rather by practicality in view of the objects to be attained hereby.

Figure 2A:
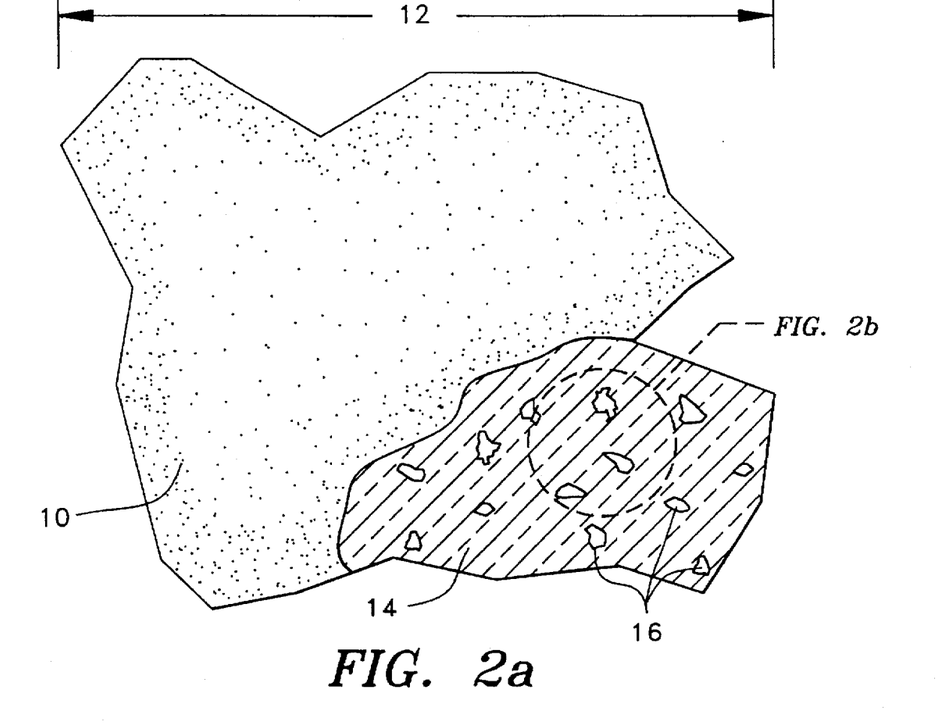
FIG. 2A depicts a particle of combeite glass-ceramic in accordance with one embodiment of the present invention. A combeite glass-ceramic particle, 10 having average dimension, 12 is shown in partial cutaway. The particle is seen to comprise a glassy, amorphous region, 14 containing numerous crystallites, 16 of combeite.
Figure 2B:
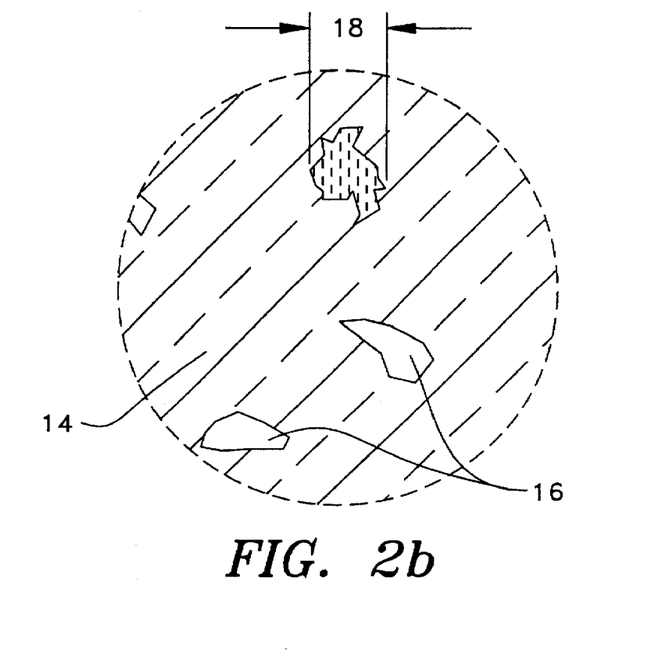
FIG. 2b is a blow up cross section of the cutaway view of FIG. 2A. The amorphous regions, 14 containing the crystallites of combeite, 16 are shown, as is an average dimension of a crystallites, 18.

FIGS. 2a and 2b depict a combeite glass-ceramic particle in accordance with the present invention. In FIG. 2a, a filler particle, 10 is depicted with a cut-away portion. In the cut-away, regions of amorphous, glassy structure 14 are shown together with crystallites 16 of combeite dispersed therethrough. FIG. 2b is a blow-up of a region of the cut-away view of FIG. 2a depicting the combeite crystallites in greater detail. It will be appreciated that FIG. 2b depicts a two-dimensional view, a transection, and that the various crystallites of combeite will be transected at various points. Thus, the dimensions of the crystallites vary depending upon where in their structure the transection occurs. Transection near an apex gives a relatively small two-dimensional view, while transection near a major access gives rise to the appearance of a large particle. An average dimension of one crystallite is shown by reference numeral 18. Likewise, average dimension, 12 of the filler particle 10 is shown in FIG. 2a.

In accordance with certain preferred embodiments of the present invention, blends of combeite glass-ceramics are employed. Thus, pluralities of combeite glass-ceramic particles, e.g. those having differing combeite levels, different particle sizes, different glass compositions, and different particle morphologies can be blended together to give rise to fillers having improved properties overall. Likewise, combeite glass-ceramic particles may be blended with other inorganic, and possibly organic filler materials to attain certain additional benefits in accordance with the invention. All that is required is that at least about 10% of inorganic filler used in hardenable compositions hereof comprise combeite glass-ceramic in accordance with the invention.

The powders, both bioactive, combeite glass-ceramic, and other fillers, are preferably blended into the resin component to achieve the desired viscosity and strength factors. The composites are easily mixed via a low speed, high sheer rotary mixer. Depending on the final filler loading, the range of preferred viscosity values can be 10,000 up to 65,000 centipoise (cps). Preferred ranges for syringe delivery are 18,000 to 35,000 cps, and most preferred, 20,000 to 30,000 cps. For putty-like consistency, the preferred viscosity range for the composite is 25,000 to 55,000 cps, with most preferred range being 35,000 to 45,000 cps. Heat generation during fingertip mixing of the high viscosity pastes can reduce the extremely high viscosities and even accelerate the polymerization mechanism.

Materials which may be included as inorganic filler in hardenable compositions in accordance with the present invention include silica, quartz, hydroxyapatite, fluorapatite, oxyapatite, Wollastonite, anorthite, calcium fluoride, agrellite, devitrite, canasite, phlogopite, monetite, brushite, octocalcium phosphate, Whitlockite, tetracalcium phosphate, cordierite, Berlinite and mixtures thereof.

Among the fillers which may be admixed with the combeite glass-ceramics of the present invention are a wide range of inorganic glasses such as barium aluminum silicate, lithium aluminum silicate, strontium, lanthanum, tantalum, etc. glasses and related materials, silica, especially in submicron sizes and other fillers as well. Silanation, which is well known per se, may also be applied to any of the fillers to improve the bonding thereof and their integration into the hardenable compositions of the invention.

Pigments, opacifiers, handling agents and other modifications may also be included in the present formulations and such adjuvants are conventionally admixed with the filler components. So long as they are compatible with the objects of the present invention, the use of such adjuvants is consistent with the present invention and contemplated hereby.

Organic filler materials which can be used in connection with the present invention include all of those set forth in the background of the invention section to this application and in the references identified therein, together with any other organic material which is consistent with the objects of this invention.

One preferred material for inclusion herein is inorganic material similar or identical in formula to Biogran™ sold by the assignee of the present invention. This has a similar overall composition to the combeite glass-ceramics of this invention, but has the presence of only very minor amounts of combeite, (less than 2% by volume) or none at all. Such material may be admixed with combeite glass-ceramics, and other inorganic and organic fillers to good effect in connection with this invention. It is preferred in some embodiments to employ particulate fillers, such as polyacrylic particles, especially bis-GMA polymers, crosslinked acrylic polymers, urethane-modified polymers, and the like. In accordance with one embodiment, interpenetrating polymer network (IPN) systems, such as are described in U.S. Pat. No. 4,396,476—Romer, et al, may be employed. It may be useful to include fibers, webs, and other structural elements in accordance with certain embodiments so long as the same do not deviate from the spirit and intended scope of the present invention.

The combeite glass-ceramic filler materials of the present invention are novel per se and may be used in any way that an inorganic filler has been known for use heretofore. Such uses include not only medical and dental uses, but also industrial use of every kind. Such filler may, therefore, be used in polymer processing, such as the formulation and manufacture of golf balls, filled plastics, reinforced cements, structural, plastic elements, modified rubbers, adhesives, paints, pigments, textiles, and as excipients, abrasives, fluidizing agents, catalysts, and, in many other systems.

A principle use of the fillers of the invention comprising combeite glass-ceramics is as part of a hardenable material for use in orthopaedic and dental restorations. In this regard, a filler in accordance with the present invention is admixed with a polymerizable matrix comprising a polymer system which is capable of hardening under the influence of heat, or photochemical energy or otherwise in a controlled fashion. It will be understood that a wide variety of polymerization systems and materials for use therein may be employed to good advantage in connection with the present invention and all such systems are contemplated hereby.

Polymerizable resins suitable for use in the practice of one or more embodiments of the present invention include a wide array of ethylenically unsaturated, and other particularly polymerizable compositions. Acrylic species are suitable. Preferably, such resins are selected from the class of acrylated polyesters. Thus, the bis-glycidyl methacrylate adduct of bisphenol-A (bis-GMA) and its other acrylic counterparts are preferred. Alternatively, the adducts of 2,2,3-trimethylhexane diisocyanate with hydroxyethyl methacrylate, hydroxypropyl methacrylate, and other hydroxyacrylic acrylic species are also preferred. Persons of ordinary skill in the art will appreciate that other acrylated polyesters may also be suited for use and that the same may be reacted with isocyanates to form urethanes useful as polymerizable species. Thus, bis-GMA may be reacted with a diisocyanate (or other isocyanate) such as hexamethylene diisocyanate, phenylene diisocyanate or a wide variety of other aliphatic and aromatic diisocyanates to provide useful polymerizable species. As disclosed in U.S. Pat. No. 4,411,625, the adducts of bis-GMA hexamethylene diisocyanate have been found to be particularly useful for restorative purposes and the same may be used here.

Methyl methacrylate, ethyl methacrylate, propyl methacrylate, and higher methacrylates, acrylates, ethacrylates, and similar species may be employed as all or part of the polymerizable materials of the hardenable compositions of the present invention. It is also possible to employ other types of polymerizable material such as epoxide compounds, polyurethane-precursor species, and a wide host of other materials. For example, other monomers useful in the production of hardenable compositions of this invention include methyl-, ethyl, isopropyl-, tert-butyloctyl-, dodecyl-, cyclohexyl-, chloromethyl-, tetrachloroethyl-, perfluorooctyl- hydroxyethyl-, hydroxypropyl-, hydroxybutyl-, 3-hydroxyphenyl-, 4-hydroxphenyl-, aminoethyl-, aminophenyl-, and thiophenyl-, acrylate, methacrylate, ethacrylate, propacrylate, butacrylate and chloromethacrylate, as well as the homologous monoacrylic acid esters of bisphenol-A, dihydroxydiphenyl sulfone, dihydroxydiphenyl ether, dihydroxybiphenyl, dihydroxydiphenyl sulfoxide, and 2,2 bis(4-hydroxy-2,3,5,6-tetrafluorophenyl)propane. Polymerizable monomers capable of sustaining a polymerization reaction such as the di-, tri-, and higher acrylic ethylene glycol dimethacrylate, diethylene glycol dimethacrylate, trimethylene glycol dimethacrylate, etc.; trimethylol propane trimethacrylate, analogous acrylates, and similar species are also useful. It is also possible to employ mixtures of two, three, and more and more polymerizable species to good effect.

It is known that bis-GMA-based polymerization systems are particularly useful in restorations within the human body. This is so for a number of well-known reasons, including general biocompatibility, absence of significant amounts of toxic products, compatible coefficients of thermal expansion, ease of use, stability, and the like. Accordingly, such materials are preferred. Bisphenol-A-glycidyl dimethacrylate (bisGMA), either with or without comonomeric species, is most preferred.

It is generally necessary to provide catalysis for the polymerizable species used in the hardenable compositions of the present invention. Such catalysts are generally of two types, heat-curing catalysts and photopolymerization initiators. Each type is well-known and any catalytic system known for restorative use may be employed so long as the same is consistent with the objects of the invention.

Heat curing catalysis is generally employed in "two-paste" systems. In such a case, a catalytic system is employed such that when two components of the hardenable composition are mixed together, the catalytic action begins, leading to hardening. This system is familiar and can be applied to a wide variety of polymerizable species including many which are suitable in the present invention. Radical initiators such as peroxides, especially benzoyl peroxide (also called dibenzoyl peroxide) are conventional, economic, and convenient. A stabilizer, such as butyl hydroxytoluene is customary. Employment of co-catalysts such as dimethyl-p-toluidine, N-N-substituted toluidine and oxylidine is conventional. In general, one of the pastes incorporates the radical initiator and stabilizer, generally a peroxide and the other paste, the accelerator, such as an amine, preferably toluidine. Curing is begun by mixing the two pastes together.

Photocuring is also a useful means for attaining hardening of compositions in accordance with the present invention. Thus, a photoinitiation system can be included with the hardenable compositions and the same caused to be activated by exposure to actinic light of a suitable wavelength. Both ultraviolet and visible photocuring systems are known for use in restorative surgery and dentistry and any such system may be employed herein. Exemplary systems are described in U.S. Pat. No. 4,110,184—Dart et al., U.S. Pat. No. 4,698,373—Tateosian et al., U.S. Pat. No. 4,491,453—Koblitz et al., and U.S. Pat. No. 4,801,528—Bennett, which are incorporated herein by reference to provide enablement for such, known systems.

A particularly useful system employs visible light curing, thus avoiding the potential danger inherent in curing with ultraviolet radiation. Visible light curing has been well-refined in the dental field, and the same may also be applied to restorations of bony tissues. Quinones, as class, find wide utility as photochemical initiators for visible light sensitizing systems, preferably when the same are admixed with tertiary amines. It is preferred that an alpha diketone (quinone) such as camphoroquinone or biacetyl be admixed with an amine reducing agent such as n-alkyl dialkanolamine or trialkanolamine.

While the hardenable compositions of the present invention are characterized as comprising polymerizable species together with filler, including combeite glass-ceramic, it will be understood that other materials may be included in such compositions. Thus, radio-opacifying agents, surface active agents, handling agents, pigments, reinforcing materials such as fibers and the like, and a wide variety of other materials may be included so long as the overall objectives of the present invention are attained.

Persons skilled in the art will appreciate that the amount of filler used in conjunction with the polymerizable materials of the present invention will depend upon several variables including the identity of the polymerizable resins and the fillers and the particle sizes of the fillers. It will be appreciated that for a given resin formulation, Judicious choice of filler type and filler particle size must be made such that an appropriate viscosity, good workability, ease of blending and eventual biocompatibility are attained.

In practice, light curable, hardenable compositions are provided in unitary form, e.g. they need not be mixed just prior to use. They are applied to the site for restoration and then exposed to visible light of a suitable wavelength to cause polymerization through intermediation of the catalyst system. Light sources and methods of applications are well known to persons of ordinary skill in the art and the same may be employed with the compositions of the present invention.

Thus, a composition of the present invention is either blended together from two "pastes", if a thermal curing system is selected, or is used as provided, if a photocuring system is elected. The same is applied to a prepared site for restoration. The restorative is then smoothed or shaped into place and the material allowed to harden either through the passage of time, in the case of a thermal curing material or through application of actinic radiation in the case of a photocuring material. After initial polymerization and resultant hardening has occurred, the restoration becomes relatively strong. It will be load bearing and capable of supporting underlying and overlying structures within the body portion thus restored.

A further aspect of the present invention is the provision of hard, shaped bodies. Thus, the hardenable compositions of the present invention may be shaped such as through conventional plastic processing technology, molding, extrusion, hand-shaping and the like, and the resulting shaped particles hardened either through the action of heat, photochemical energy or otherwise. It is thus, possible to provide a whole host of shaped bodies formed from the materials of the invention which contain combeite glass-ceramic. These shaped bodies may be used in a wide variety of applications, especially in surgery and dentistry, where their properties of biocompatibility, osteogenic stimulation, and inherent strength will be found to be beneficial.

For example, pins, screws, or rods may be formulated out of hardenable compositions of the invention through conventional extrusion or molding and caused to be hardened. These pins, screw and rods may be used wherever conventional pins, screws, or rods used in orthopaedic surgery are presently employed to provide strength and stability to injured joints, fractured bone, and otherwise. In use, such pins, screws, and rods are inserted into a prepared location and cemented into place. Unlike prior, generally metallic, pins or rods, however, the materials of the present invention are inherently biocompatible and, indeed, osteostimulatory. This is enhanced when the cement used to affix the object rod to the bony structure is selected to be a hardenable composition of the present invention as well. As will be appreciated, adjustment of viscosity for the material to serve as a cement for the pin, screw, or rod can make it convenient to use this system in the repair of bony structure. The result is that the entire repair is made using only biocompatible and, indeed, osteostimulatory material; no metal at all need be employed.

A further use of the hardened materials of the present invention can be found in endodontics. It is conventional to employ "points" for the restoration of root canals and the like. Such points are conventionally silver, gutta percha, or certain other materials. To restore a root canal, access to the root canal of a diseased tooth is obtained through the enamel and dentin of the tooth and a portion of the nervous, bony, and other tissue of the root canal is removed through the use of a number of conventional instruments. The actual preparation of root canals for restoration forms no part of the present invention and all such aspects of the procedure are well understood by persons skilled in the art.

A prepared root canal must then be filled. Conventionally, this is attained by placing silver or gutta percha "points" into the prepared canal and causing the same to be compacted into the space to be restored. It is important that no leakage be experienced around the apical foramen or subsequent reinfection may occur. This process can be traumatic to the patient and is difficult to perform in practice.

In accordance with the present invention, endodontic "points" can be prepared using the hardened compositions of the invention. These can then be inserted into the excavated space of a root canal along with quantities of hardenable composition in accordance with the present invention and the same caused to harden in situ. Substantially complete filling of the prepared root canal space can be attained and the osteostimulatory characteristic of the present materials can give rise to improved biocompatibility, and integration of the restoration into the patient's bony structure, ensuing good results.

Figure 3A:
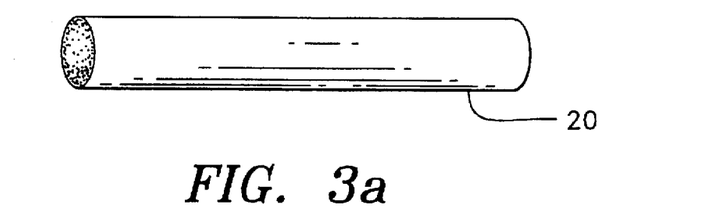
FIGS. 3a, 3b, 3c and 3d depict shaped articles produced from the hardenable compositions of the present invention. The article depicted in FIG. 3a is a rod or pin which can be used in orthopaedic surgery.
Figure 3B:
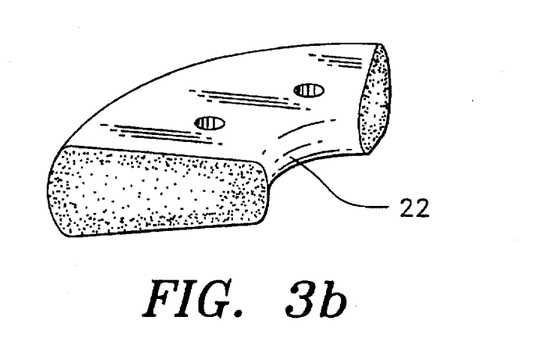
Figure 3C:
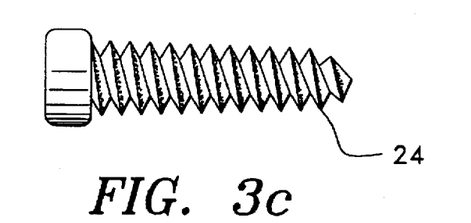
Figure 3D:
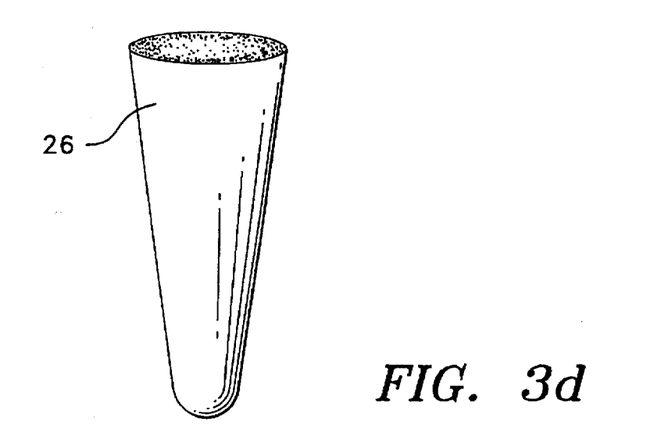

FIG. 3A depicts a rod useful for orthopaedic restorations as described above. FIG. 3B shows a spacer for insertion into a vertebral space during spine fusion. FIG. 3C is a screw formed from hardened composition of the invention while FIG. 3D depicts a dental point.

Composites of the present invention may be used in a wide variety of restorative and surgical procedures including those involving bone tissue subject to large forces. One example is the repair or fusion of vertebrae of the spine. A composite material can be placed in or near the spine via syringe delivery and caused to polymerize in situ. The resulting, hardened material provides load-bearing stability and micromechanical bonding to vertebrae or other bony material. After some time in the body, tissue and bone attachment become augmented through the biological interfacial chemical bond that eventually forms a hydroxy apatite biologic interfacial bond between tissue, bone, and the composite.

Hardened materials, such as vertebral spacers of all sizes and shapes can be prefabricated and caused to polymerize outside the body in order to maximize design features necessary for surgical restoration in vivo. For example, a pre-formed and hardened vertebral spacer can be placed into a vertebral space and affixed thereto with the aid of wire, rods, pins, screws, or adhesives in accordance with the present invention or otherwise. A spinal cage prefabricated from the material of the present invention offers familiarity of process, stability and implementation together with autogenous bone grafting to the end that a number of flexible applications for spinal and other such restorations obtain.

The materials of the present invention can also be employed in dentistry and orthopaedics in all of those circumstances where polymethyl methacrylate is presently employed. Once an implantation sight has been prepared, syringe delivery of a low-viscosity version of composites of the present invention can be expressed to fill the void. If desired, an implant may be used in conjunction with polymerizable material of the present invention, such implant being either metal, gutta percha, ceramic, polymer, or, indeed, a hardened material in accordance with this invention. Subsequent setting of the polymerizable material yields a gross restoration suitable for finishing, further restorative application, or otherwise.

A particular advantage of the present methodology is that after healing of the situs of the restoration or implant, the implanted material will begin to adhere chemically to bone tissue interface, increasing the strength and toughness of the implant system.

The materials of the present invention are particularly useful for repairing failed implants, especially in dental applications. After a patient has spent months or years in therapy directed to the stabilization of a dental implant, it's failure is psychologically and physically catastrophic. The use of composite materials such as those of the present invention permits removal of the failed implant, refilling of the maxillary or mandibular void with bioactive composite either in syringable or in putty form, followed by immediate replacement of the implant. Rapid adjustment of position, setting, and the like, together with minimal healing time is an attractive feature of the invention. It is also possible to stabilize an implant which is in the process of failing through the application of materials in accordance with the present invention. The injection of a composite material in accordance with this invention is particularly suited to this application since the same bonds to tissues, metal, and itself together with numerous other composite materials, thus providing tremendous flexibility for such restorations.

Materials of this invention are also particularly suited to the repair of comminuted fractures. In such a case, a traumatic injury has led to crushed or fragmented bone and a non-lead bearing graft material would not be useful for its repair. At present, the use of metal plates and rods is the only viable option. The present invention can be used to reassemble bone fragments since the present materials can be formulated into putty for this purpose. Alternatively, photo-curing materials may be used to cause tackification and curing in a short period of time thus to facilitate the reassembly of such fractures. It is also possible to employ hardened materials in accordance with the present invention, or traditional metal or ceramic bones, pins, plates, and the like for such restorations. The rapid load bearing capability of the materials of the present invention along with their bioactivity confer particular advantages to the present system.

A further example of the utility of the materials of the present invention in orthopaedics involving great stresses and procedural difficulties involves bipolar hip replacement or revision. In such a case, implant fixation on the femural stem side is simple, however, the acetabular cup attachment is very difficult, especially in revision cases. With the use of pins, the acetabulum can be looted with compositions of the present invention to make up for lost bone of the acetabulum. Immediate function is critical to this application and the load bearing ability of the present materials indicates it for such use. The biological bonding of the materials of the present invention will enhance strength and toughness in such procedures and prevent further absorption of existing bone. Revision surgery for a failed bipolar hip replacement is typically an emergency requiring deliverable, flexible, and functional materials such as those of the present invention.

Figure 4:
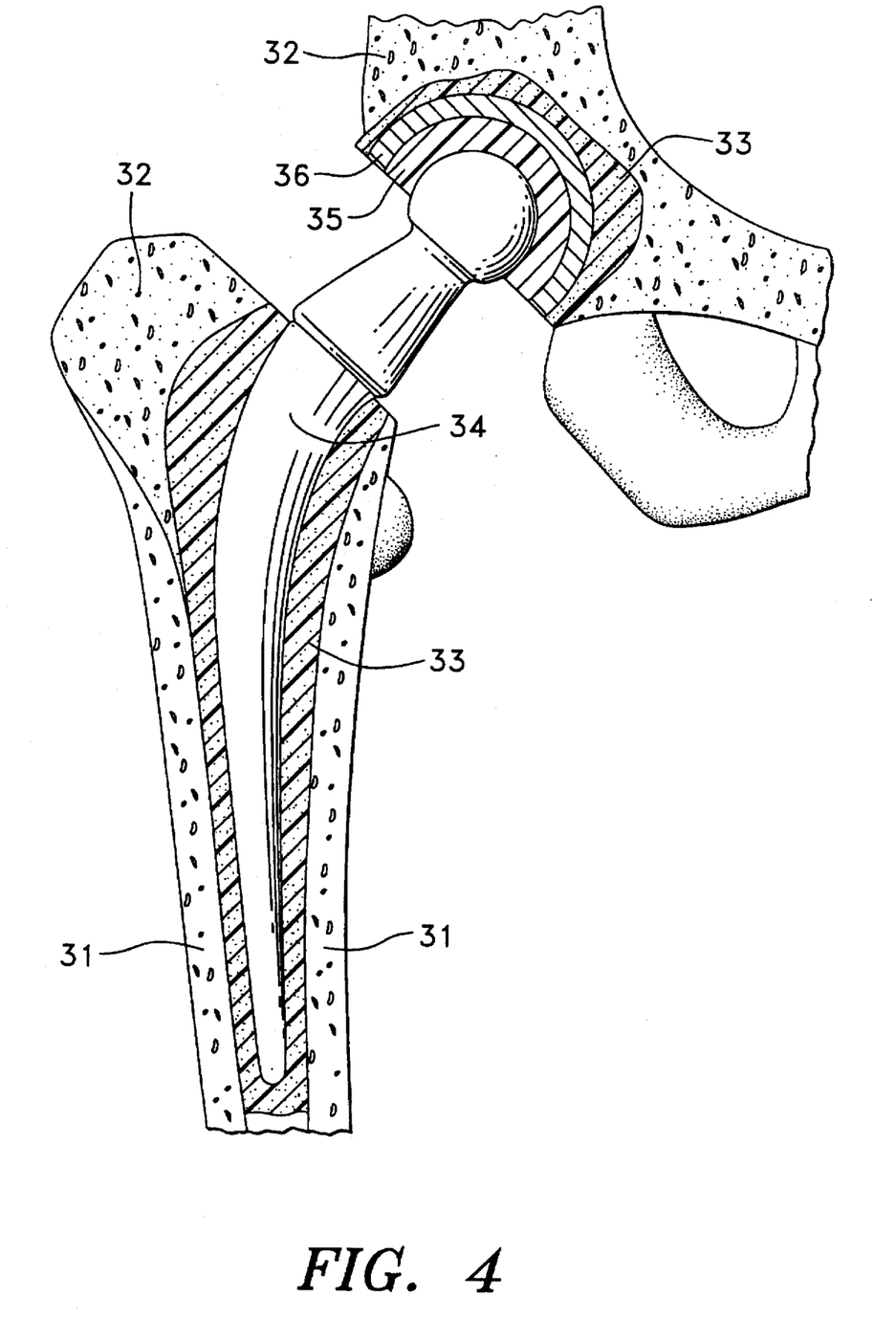
FIG. 4 depicts a bipolar hip replacement using material of the invention.

FIG. 4 shows a bipolar hip replacement. The femur, having cortical bone, 31 and spongeous bone, 32 is implanted with a prosthesis 34, cemented in place with composite of the invention, 33. On the acetabular side, a femural head articulation surface, 36 is cemented to a prepared cavity with material of the invention, 33. A high weight polyethylene cup, 35 is used to facilitate articulation with the head of the prosthesis. FIG. 3 shows a spacer for insertion into a vertebral space during spine fusion.

The present invention is limited solely by the appended claims and the proposed mechanism of action is not to be construed as limiting in any way. It is believed, however, that the particles of combeite glass-ceramic of the invention are particularly beneficial for biological restorations due to their unique structure and properties. When combeite crystallites form, the remaining glass is depleted in some elements and enriched in others. The residual glass matrix after combeite crystallization is high in CaO and $P_2O_5$, which gives rise to a high degree of bioactive interaction with adjacent tissue. As the volume fraction crystallized increases, the glass phase decreases. The nature of this dissolution creates a mineral rich surface on the composite that allows for interdigitation of surrounding bone tissue. The quick reaction of combeite glass-ceramic and surface mineralization of the composite may be self-limiting, therefore retaining the internal strength of the composite.

In some cases, composite surfaces on the interior may not participate in the biological reactions and are thus, behave as a fully strengthened composite. The bisphenol-A glycidyl dimethacrylate (BisGMA) resin matrix can be blended with other monomers such as triethylene glycol dimethacrylate (TEGDMA), diurethane dimethacrylate (DUDMA), or ethoxylated bisphenol-A-glycidyl dimethacrylate (BisEMA). The working time and set time can easily be adjusted with the levels of amine in one component A and the benzoyl peroxide and butyl hydroxytoluene in the other. The average working time desired is 3 to 6 minutes with immediate set thereafter. Full composite strength is preferably achieved within 1.5 to 2 hours.

The unique bioactive bone grafting composites of this invention are suited for implant fixation and repairs to viable tissues and bone due to their ease of delivery and placement, low heat generation on polymerization, low shrinkage, as well as immediate fixation, adherence, and load bearing. The unique surface interaction leads to a bonded bioactive surface. The synergy between the combeite glass-ceramic filler and the resin matrix is believed to generate a reactive bone bonding resin-gel layer that is ultimately converted to a resin-hydroxy apatite layer.

The self limiting biologic reaction makes the composite ideal for dual functioning. Thus, it is at least surface bioactive while internally functioning as a structural composite. This dual functioning of this composite makes it suitable for bone fracture repair where immediate fixation and load bearing is critical. The lower modulus matrix affords shapeability and transfers the stress to the higher modulus filler. The modulus of these composites (5–50 GPa) is closer to that of natural bone (7–20 GPa) than PMMA alone (3–5 GPa) or metal (100–200 GPa). Having an elastic modulus comparable to bone avoids damaging stress shielding. The fracture toughness of the entire system is enhanced due to the bond strength to the implant (metal and ceramic) surfaces and to bone. The intimate surface adhesion and chemical bonding eliminates micromotion, aseptic loosening, and maximizes the stress transfer for optimum load bearing characteristics.

Once in contact with the physiologic environment, the set composite reacts with the fluids of the body. The serum and physiologic fluids diffuse into the permeable structure of the reinforced composite and reacts with the bioactive phases. Similarly to surface active bioceramics, the reactant phases transport $Ca^{+2}$, and $PO_4^{-3}$ ions to the surface of the composite. Due to the supersaturation of the surrounding surface fluid, the slight increase in Ph, and the active surface silanols and other resin hydroxyls, the entire surface of the composite and some 100 to 200 micrometers into the composite is believed to be covered with a gel layer rich in CaO and $P_2O_5$. This diffuse layer of resin-CaO-$P_2O_5$ forms the precursor for the conversion to the bone mineral, hydroxylapatite. The nature of the resin matrix that allows ion migration for bioactivity also benefit drug delivery from an incorporated medicament.

Depending on the degree of reaction of the bioactive filler, the particle size and the filler loading, interdigitation of surrounding structures on the partially resorbable surface can occur. If the particle size of the bioactive filler is relatively large, the reaction of that particle leaves a large channel for bone cells, macrophages, and vascularization. On a microscale, up to 200 to 300 micrometers, interdigitation of viable bone forming tissues can impregnate the composite surface with bone mineral. This micromechanically and chemically bonded interface is self limiting and strengthens as the interface crystallizes to form bone mineral, hydroxy apatite. The time for these events can take up to 8 weeks, but the strength of the hardened composite allows for immediate function. Improved bonding at the biologic interface promotes further solidification and long term stability.

Preferred resin systems are composed of two pastes A & B. In one embodiment, paste A resin is comprised of 40–60% by weight bisphenol-A glycidyl dimethacrylate (BisGMA), 10–45% by weight triethylene glycol dimethacrylate (TEGDMA), 0–40% by weight diurethane dimethacrylate (DUDMA), 0.2–3.5% by weight N,N-dimethyl-p-toluidine or other N,N-dialkyl anilines or N,N-dialkyl toluidines, and 0–1.5% by weight butylhydroxytoluene (BHT) or other free radical stabilizers. Paste B resin is comprised of 40–60% by weight bisphenol-A-glycidyl dimethacrylate (BisGMA), 10–45% by weight triethyleneglycol dimethacrylate (TEGDMA), 0–40% by weight diurethane dimethacrylate (DUDMA), 0.1–3.0% by weight benzoyl peroxide (BPO) or other organic peroxides, and 0–2% by weight butylhydroxytoluene (BHT) or other free radical stabilizers.

Various combinations of amine:BPO:BHT will yield specific working and set times. Within the composition variables given above, the 2.25:1:0.12 ratio gives the preferred long work time of 5 minutes and the slow set time of 8 to 10 minutes. The more preferred 3 minutes working time and 5 to 7 minutes set time is obtained with a 2.5:1:0.1 amine:BPO:BHT ratio. Each set character will depend on the mass of material used, energy imparted upon mixing, and the temperature of the body (normally 37° C.) at the implant site.

The filler level of paste A & B can vary from 65 to 85% by weight total filler content with the preferred bioactive glass-ceramic (Combeite glass-ceramic, CGC) content ranging from 10 to 99% by weight of that filler. It is preferred that the particle size distribution be broad, bimodal, or preferably trimodal, also of which being less than about ~300 micrometers, with less than 5% by weight being sub 0.1 microns sized.

Relatively low viscosity, syringable pastes are best suited for the filling of bony defects, fracture repair, and implant fixation and revision. Syringable pastes flow to fill voids, and crevices, and adhere tightly to the surface of the bone, tissue, or implant. Flowability can be important for tight adherence and removal of micromotion when implant securing is being achieved. The lack of implant motion can reduce inflammation and determine the success of the implant system over time. Higher viscosity pastes are desirable for larger, load bearing bone defects and easily accessible fracture sites. A "putty" can be manipulated, sculpted and cured in place with immediate high strength capability. Oncological bony defects are well-suited for highly loaded, highly bioactive composites. The use of hand mixed pastes can also facilitate the addition of medicaments, antibiotics, or bone growth factors.

The resulting composite has a permeable surface and 3-dimensional network that allows the bioactive fillers to react with the physiologic environment to form an interdigitated, diffuse interface layer comprised of resin-$CaO$-$P_2O_5$. This layer is the precursor to bone mineral adhesion and formation. The micromechanical interlocking of bone tissue and the surface of the composite strengthens as the chemical bonds form and crystallize into bone mineral (HAp). The degree of interdigitation and the gel layer is controlled by the amount of bioactive filler and the particle size distribution of that filler.

EXAMPLE 1

Combeite Glass-Ceramic

A blend of 33.9% silica, commonly denominated "candle quartz", 30.98% sodium carbonate, 26.36% calcium carbonate and 8.68% calcium hydrogen phosphate ($CaHPO_4$) were melted together in a covered, platinum crucible in a 1 kilogram batch in a Globar™ furnace under ordinary atmosphere at a temperature between about 1200° and 1400° C. for 12 hours. The resulting homogeneous melt was cast onto a graphite plate and allowed to cool to room temperature. The solid body thus formed was crushed, comminuted in a ball-mill, and subjected to a ball mill or jaw crusher and then series of screens to provide size segregation.

The ensuing particulate, combeite glass-ceramic was comprised of particles having irregular morphologies evidencing the fracturing and comminuting processes described above. The morphologies include jagged edges, rough prominences, irregular declivities, and similar structures. Combeite glass-ceramic particles were obtained having 5-10 volume percent combeite in the form of microcrystalline regions—crystallites—as determined by X-ray diffraction spectroscopy. The amount of combeite in the combeite glass-ceramics prepared in accordance with this example can be varied by varying the time heated at Tc or the temperature and time held above Tc. It is, thus possible to prepare combeite glass-ceramics in particulate form having combeite compositions crystallites ranging from 2% to 70% by volume.

The overall composition the combeite glass-ceramic particles produced in accordance with this method, including both the amorphous regions and the combeite crystallites, was found to be 45% by weight silica, 24.5% sodium oxide, 24.5 calcium oxide and 6% $P_2O_5$.

EXAMPLE 2

Combeite Glass-Ceramic, Frit Method

The blend of silica, sodium carbonate, calcium carbonate and calcium hydrogen phosphate of Example 1 was melted as before. Rather than allow the same to cool as a body on a substrate, the melt was poured into distilled water to yield a frit. This frit was crushed to give rise to particulate combeite glass-ceramic having highly irregular surface morphologies. The overall composition of the combeite glass-ceramic is the same as is found in the product of Example 1, however the combeite crystallite composition is variable. It is possible to modify the amount of combeite in the combeite glass-ceramic in accordance with this protocol via time, temperature profile adjustment. Particle size ranges may also be selected through conventional means.

EXAMPLE 3

Paste-Paste Restorative

An acrylic resin-based paste-paste bone restorative composition is prepared including combeite glass-ceramic in accordance with this invention. A first component was prepared consisting of:

| | |
|---|---|
| bisphenol-A-glycidyl dimethacrylate (BisGMA) | 55 parts by weight |
| triethyleneglycol dimethacrylate (TEGDMA) | 45 parts by weight |
| butylhydroxytoluene (BHT) | 0.04 parts by weight |
| N,N-dimethyl-p-toluidine (DMEPT) | 1.0 parts by weight |
| dihydroxyethyl-p-toluidine (DHEPT) | 1.5 parts by weight |

An inorganic filler blend is prepared comprising the following components:

| | |
|---|---|
| Combeite glass-ceramic having between 2 And 5% by volume combeite in a particle size less than about 50 microns | 50 parts by weight |
| Combeite glass-ceramic having between 5 and 50% by volume combeite in particle sizes less than about 50 microns | 10 parts by weight |
| fumed silica having particle sizes less than about 1 micron and treated with 2% of chloro trimethylsilane | 8 parts by weight |
| barium-alumina silica glass (available from Scientific Pharmaceuticals, Inc. under the trademark IV 2324) having particle sizes less than 50 microns | 32 parts by weight |

The foregoing inorganic filler material is sieved to ensure that at least 95% by weight of the inorganic, particulate filler is less than about 50 microns in size.

The resin blend, in the amount of 35% by weight, is combined with the above-described filler blend, 65% by weight, and thoroughly mixed to result in a first component of a two-part paste restorative composition. The viscosity of this first component is approximately 15,000 centipoises.

A second component of the two-component paste restorative composition is prepared from resin and filler materials as follows:

A resin composition comprising the following materials was blended together:

| | |
|---|---|
| bisphenol-A-glycidyl dimethacrylate | 55 parts by weight |
| triethylmeglycol dimethacrylate | 45 parts by weight |
| butylhydroxytoluene | 0.04 parts by weight |
| benzoyl peroxide (BPO) | 1.0 parts by weight |

This resin component, in the amount of approximately 35 weight percent, was blended with 65 weight percent of the filler blend described heretofore. The resulting, second component of the two-paste system has a viscosity of approximately 15,000 centipoises.

The first and second components, when blended together, undergo a peroxide-catalyzed, thermal reaction to result in hardening of the blended composition. The initial viscosity of the blended materials is approximately 15,000 centipoises, a viscosity which is amenable to delivery via wide-mouth syringe. The working time is between about 3 and 5 minutes at 22° C. After this time, substantial hardening begins. The hardened material is fully compatible with bone tissue and dental structures.

The composition of this example sets hard within about 5 minutes to a load bearing, high strength form. The composite adheres immediately to metal, forming a strong bond, as well as adhering to the shape of a cavity being filled. The material is highly formable, shapable and easily delivered by a syringe delivery system. The composite is believed to be bioactive in that, upon contact with physiologic fluids and blood sera, there is suspected to be a biologic interface which forms and eventually hardens.

EXAMPLE 4

Paste-Paste Restorative

A resin formulation is prepared from the following components:

| | |
|---|---|
| bisphenol-A-glycidyl dimethacrylate | 50 parts by weight |
| triethyleneglycol dimethacrylate | 15 parts by weight |
| diurethane dimethacrylate CAS 411 37-6-4 available from Rohm Tech as MHOROMER 6661-0 | 35 parts by weight |
| butylhydroxytoluene | 0.04 parts by weight |
| N,N-dimethyl-p-toluidine (DMEPT) | 0.75 parts by weight |
| dihydroxyethyl-p-toluidine (DHEPT) | 1.5 parts by weight |

An inorganic filler blend is prepared from the following materials:

| | |
|---|---|
| Combeite glass-ceramic having between 2 and 5% by volume combeite and particle sizes less than about 50 microns | 50 parts by weight |
| Combeite glass-ceramic particles having between 5 and 50% by volume combeite and particle sizes less than about 50 microns | 5 parts by weight |
| Combeite glass-ceramic having more than 50% by volume combeite and particle sizes less than about 50 microns | 5 parts by weight |
| silane treated fumed silica having particle sizes less than 1 micron | 8 parts by weight |
| barium alumina silicate glass having particle sizes less than about 50 microns | 27 parts by weight |
| dicalcium phosphate dehydrate | 5 parts by weight |

The foregoing inorganic filler material is sized to ensure that at least 95% of the particles have sizes less than about 50 microns. A first paste is prepared from 65% of inorganic filler blend and 35% of the foregoing resin composition.

A second resin composition comprising:

| | |
|---|---|
| bisphenol-A-glycidyl dimethacrylate | 50 parts by weight |
| triethyleneglycol dimethacrylate | 15 parts by weight |
| diurethane dimethacrylate | 35 parts by weight |
| butylhydroxytoluene | 0.08 parts by weight |
| benzoyl peroxide | 1.0 parts by weight | is blended with the inorganic blend of this example such that the resin component comprises 35% and the filler composition comprises 65% by weight of the material. The resulting composition forms a second paste capable of catalyzing a hardening reaction.

Each of the pastes has a viscosity of approximately 18,000 centipoises, and is suitable for syringe delivery. When blended together, the composite has a working time between about 5 and 8 minutes at 22° C.

It is expected that the generally higher crystallinity of the combeite glass-ceramic of this example gives rise to a somewhat slower bioactivity. The release of calcium and phosphate ions is compensated for by the addition of DCPD which give rise to a slightly overall increase in the viscosity of the material.

EXAMPLE 5

Paste-Paste Restorative

A resin blend is prepared from:

| | |
|---|---|
| bisphenol-A-glycidyl dimethacrylate (BisGMA) | 45 parts by weight |
| triethyleneglycol dimethacrylate (TEGDMA) | 25 parts by weight |
| diurethane dimethacrylate (DUDMA) | 30 parts by weight |
| butylhydroxytoluene (BHT) | 0.06 parts by weight |
| N,N-dimethyl-p-toluidine (DMEPT) | |
| dihydroxyethyl-p-toluidine (DHEPT) | 2 parts by weight |
| A filler blend is prepared from: | |
| combeite glass-ceramic (2 < 5% by volume combeite) | 50 parts by weight |
| combeite glass-ceramic (5 < 50% by volume combeite) | 5 parts by weight |
| combeite glass-ceramic (>50% by volume combeite) | 0 parts by weight |
| silane treated fumed silica (<1 micrometer) | 5 parts by weight |
| silane treated BaO—$B_2O_3$—$Al_2O_3$—$SiO_2$ glass (<50 micrometers) | 20 parts by weight |
| dicalcium phosphate dihydrate (DCPD) | 20 parts by weight |

All of the combeite glass-ceramic powder is less than 50 micrometers in size. A first paste having 65% by weight filler blend is formed and found to have a low viscosity syringe delivery.

A resin blend for a second paste was prepared from:

| | |
|---|---|
| bisphenol-A-glycidyl dimethacrylate (BisGMA) | 45 parts by weight |
| triethyleneglycol dimethacrylate (TEGDMA) | 25 parts by weight |
| diurethane dimethacrylate (DUDMA) | 30 parts by weight |
| butylhydroxytoluene (BHT) | 0.1 parts by weight |
| benzoyl peroxide (BPO) | 1.0 parts by weight |

-continued

| The filler for this paste consists of: | |
| --- | --- |
| Combeite glass-ceramic (CGC) (2 < 5% by volume combeite) | 50 parts by weight |
| CGC (5 <50% by volume combeite) | 5 parts by weight |
| CGC (>50% by volume combeite) | 0 parts by weight |
| silane treated (ST) fumed silica (<1 micrometer) | 5 parts by weight |
| silane treated BaO—$B_2O_3$—$Al_2O_3$—$SiO_2$ glass (<50 micrometers) | 20 parts by weight |
| dicalcium phosphate dihydrate (DCPD) | 20 parts by weight |

All of the combeite glass-ceramic powder is less than 50 micrometers in size. The filler content of the second paste is adjusted to 65% by weight for a syringe. The working and set time of the above composite at room temperature (22° C.) is 7 and 10 minutes, respectively. The crystalline combeite glass-ceramic phase and the DCPD increases the release of $Ca^{+2}$ and $PO_4^{-3}$ ions.

What is claimed:

1. A hardenable composition comprising
   a polymerizable matrix; and
   inorganic filler, at least 10 percent of said filler comprising combeite glass-ceramic having at least about 2 percent by volume of regions of combeite and irregular morphology.

2. The composition of claim 1 wherein combeite comprises at least about 3 percent by volume of said combeite glass-ceramic.

3. The composition of claim 1 wherein combeite comprises at least about 5 percent by volume of said combeite glass-ceramic.

4. The composition of claim 1 wherein combeite comprises at least about 10 percent by volume of said combeite glass-ceramic.

5. The composition of claim 1 wherein combeite comprises between about 5 and 50 percent by volume of said combeite glass-ceramic.

6. The composition of claim 1 wherein combeite comprises between about 10 and 20 percent by volume of said combeite glass-ceramic.

7. The composition of claim 1 wherein said combeite glass-ceramic is present in the form of heterogeneous particles.

8. The composition of claim 7 wherein at least 95% by weight of said particles have particle sizes greater than about 0.1 micron.

9. The composition of claim 7 wherein at least 95% by weight of said particles have particle sizes greater than about 0.2 micron.

10. The composition of claim 7 wherein at least 95% by weight of said particles have particle sizes less than about 300 microns.

11. The composition of claim 7 wherein at least 95% by weight of said particles have particle sizes less than about 100 microns.

12. The composition of claim 7 wherein at least 95% by weight of said particles have particle sizes between about 0.2 and 300 microns.

13. The composition of claim 7 wherein at least 95% by weight of said particles have particle sizes between about 0.2 and 100 microns.

14. The composition of claim 7 wherein at least 95% by weight of said particles have particle sizes between about 0.5 and 50 microns.

15. The composition of claim 1 wherein the combeite glass-ceramic filler has an X-ray diffraction spectrum substantially in accordance with FIG. 1.

16. The composition of claim 1 wherein said combeite glass-ceramic is present in the form of heterogeneous particles having an irregular morphology.

17. The composition of claim 1 wherein said combeite glass-ceramic filler is a blend.

18. The composition of claim 1 wherein said inorganic filler further comprises at least one additional inorganic material.

19. The composition of claim 18 wherein said additional inorganic material is hydroxyapatite, fluorapatite, oxyapatite, Wollastonite, anorthite, calcium fluoride, agrellite, devitrite, canasite, phlogopite, monotite, brushite, octocalcium phosphate, Whitlockite, tetracalcium phosphate, cordierite, Berlinite or mixtures thereof.

20. The composition of claim 1 wherein said polymerizable matrix comprises acrylic species.

21. The composition of claim 1 wherein said polymerizable matrix comprises a bisphenol-A dimethacrylate.

22. The composition of claim 21 wherein said bisphenol-A dimethacrylate is a bisphenol-A glycidyl dimethacrylate.

23. The composition of claim 22 wherein said dimethacrylate has been urethane modified.

24. The composition of claim 1 wherein the polymerizable matrix comprises a heat- or photo-polymerizing catalyst.

25. The composition of claim 24 wherein said catalyst comprises a quinone in admixture with a tertiary amine.

26. The composition of claim 24 wherein said catalyst comprises a peroxide.

27. The composition of claim 1 having a viscosity amenable to spatulation or delivery via a wide mouth syringe.

28. The composition of claim 27 having a viscosity between about 5,000 and 75,000 centipoises.

29. The composition of claim 1 wherein the regions of combeite comprise crystallites.

30. The composition of claim 1 wherein said combeite glass-ceramic filler has
    from 40–55% by weight $SiO_2$
    from 10–32% by weight $Na_2O$
    from 4–12% by weight $P_2O_5$, and
    from 10–32% by weight CaO.

31. The composition of claim 1 wherein said combeite glass-ceramic filler has
    from 42–48% by weight $SiO_2$
    from 14–28% by weight $Na_2O$
    from 5–10% by weight $P_2O_5$, and
    from 20–29% by weight CaO.

32. The composition of claim 1 wherein said combeite glass-ceramic filler has
    about 45% $SiO_2$; 24.5% $Na_2O$; 24.5% CaO and 6% $P_2O_5$.

33. A hardenable, biocompatible restorative composition comprising
    at least one acrylic monomer;
    a polymerization catalyst; and
    inorganic filler, at least 10 percent of said filler comprising combeite glass-ceramic having at least about 2 percent by volume of regions of combeite crystallites.

34. A method for the preparation of a hardenable composition comprising blending together at least one acrylic monomer, at least one polymerization catalyst and inorganic filler, at least 10 percent of said filler comprising combeite glass-ceramic having at least about 2 percent by volume of regions of combeite.

35. The method of claim 34 wherein said acrylic monomer comprises at least one bisphenol-A methacrylate.

36. The method of claim 34 wherein said acrylic monomer comprises bisphenol-A glycidyl dimethacrylate.

37. The method of claim 34 wherein combeite comprises at least about 3 percent by volume of said combeite glass-ceramic.

38. The method of claim 34 wherein combeite comprises at least about 5 percent by volume of said combeite glass-ceramic.

39. The method of claim 34 wherein combeite comprises at least about 10 percent by volume of said combeite glass-ceramic.

40. The method of claim 34 wherein combeite comprises between about 5 and 50 percent by volume of said combeite glass-ceramic.

* * * * *